United States Patent [19]

Bahler

[11] Patent Number: 5,282,868
[45] Date of Patent: Feb. 1, 1994

[54] PROSTHETIC ARRANGEMENT FOR A COMPLEX JOINT, ESPECIALLY KNEE JOINT

[76] Inventor: André Bahler, Kapfsteig 44, CH-8032 Zurich, Switzerland

[21] Appl. No.: 898,141

[22] Filed: Jun. 15, 1992

[30] Foreign Application Priority Data

Jun. 17, 1991 [CH] Switzerland ............ 01797/91
Jun. 17, 1991 [CH] Switzerland ............ 01798/91

[51] Int. Cl.$^5$ ............................................. A61F 2/38
[52] U.S. Cl. ............................................. 623/20
[58] Field of Search ........................ 623/16, 18, 20

[56] References Cited

U.S. PATENT DOCUMENTS

| | | | |
|---|---|---|---|
| 4,085,466 | 4/1978 | Goodfellow et al. | 623/20 |
| 4,207,627 | 6/1980 | Cloutier | 623/20 |
| 4,309,778 | 1/1982 | Buechel et al. | 623/20 |
| 4,340,978 | 7/1982 | Buechel et al. | 623/20 |
| 4,353,136 | 10/1982 | Polyzoides et al. | 623/20 |
| 4,470,158 | 9/1984 | Pappas et al. | 623/20 |
| 4,728,332 | 3/1988 | Albrektsson | 623/20 |
| 4,950,297 | 8/1990 | Elloy et al. | 623/20 |
| 5,007,933 | 4/1991 | Sidebotham et al. | 623/20 |
| 5,011,496 | 4/1991 | Forte et al. | 623/20 |

FOREIGN PATENT DOCUMENTS

1567007 5/1980 United Kingdom .

OTHER PUBLICATIONS

"New Jersey Tricompartmental Total Knee System".
"A Manual of the Oxford Knee", published by OEC Orthopaedic Ltd. Bridgend, South Glamorgan, United Kingdom.

*Primary Examiner*—David Isabella
*Attorney, Agent, or Firm*—Frishauf, Holtz, Goodman & Woodward

[57] ABSTRACT

To permit movement of coupling elements (13, 13a, 13b) which carry joint surfaces (21) congruent with condylar portions (19) of the prosthesis, the coupling elements are slidable in guide tracks (35), which are curved, and are widened at their terminal portions. The coupling elements have elongated engagement ribs which fit into the guide track groove, with minimum clearance and play at the narrowest, central portion of the guide groove, while permitting limited twisting as well as sliding movement due to the widened regions of the guide track at its end region. The position of guide track-rib can be reversed, if desired. The elements slide on a slide surface and can be retained, for example by an interlocking connection, such as a dovetail.

23 Claims, 16 Drawing Sheets

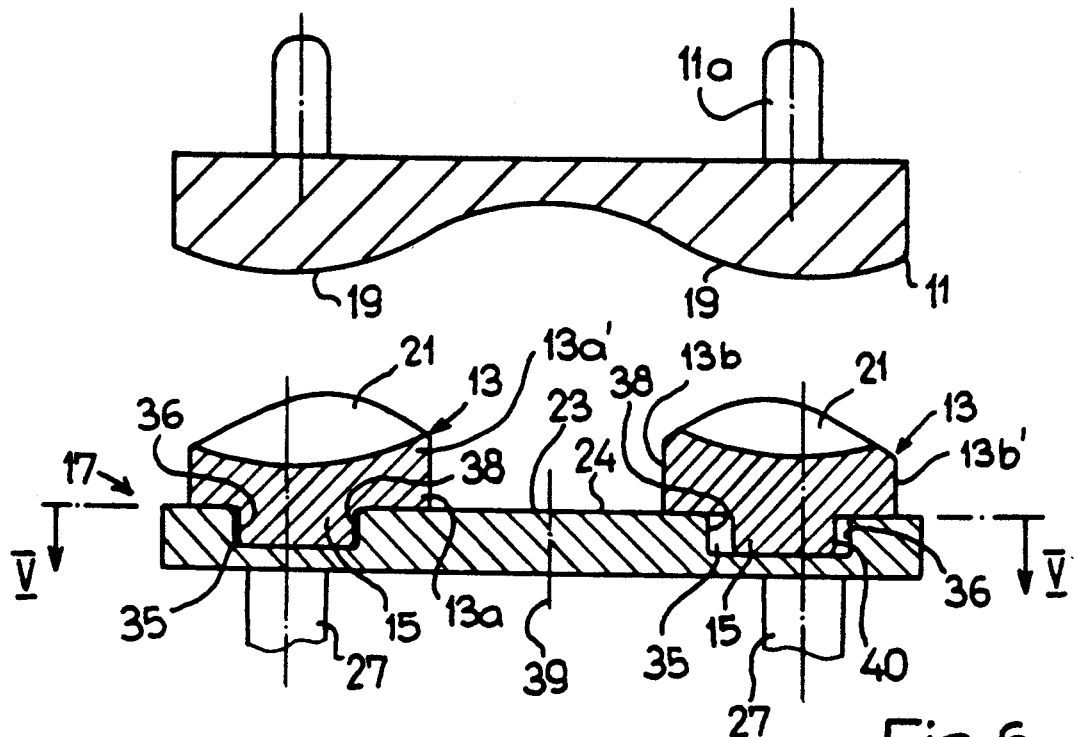
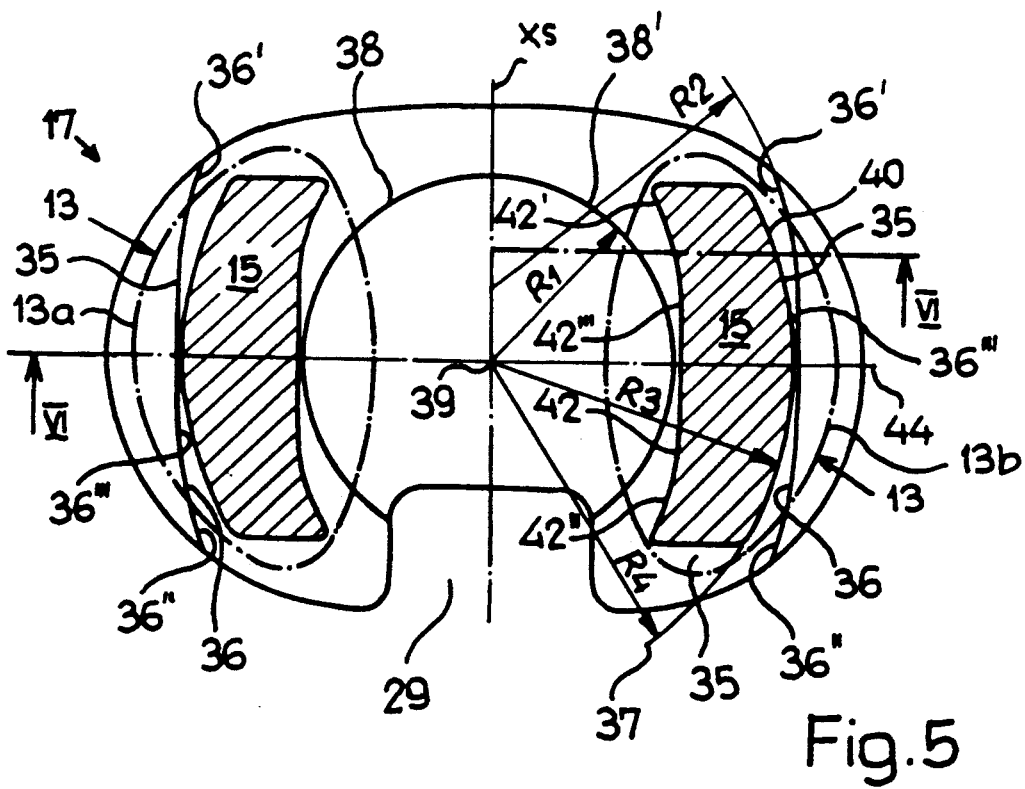
Fig. 6
Fig. 5

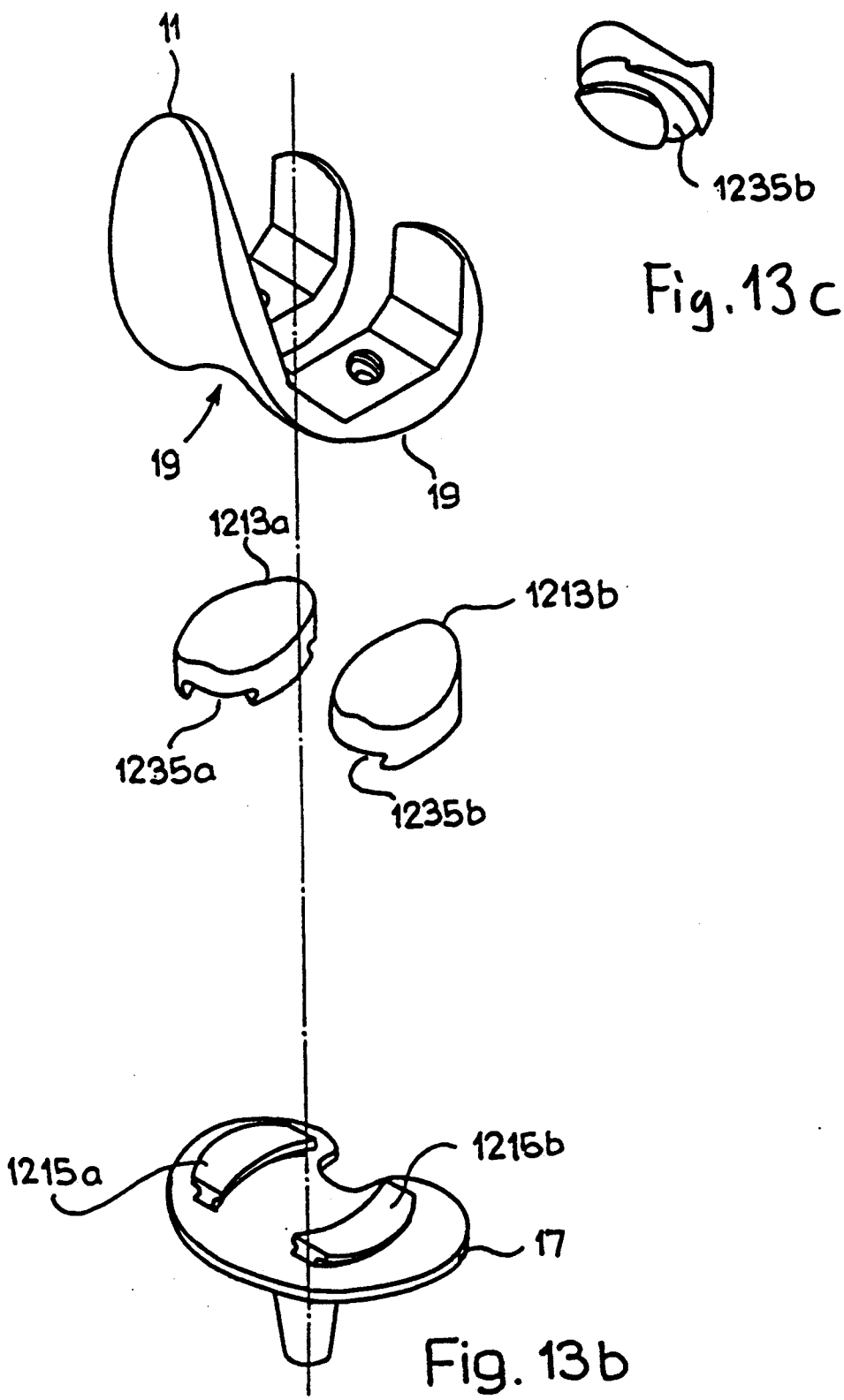

PROSTHETIC ARRANGEMENT FOR A COMPLEX JOINT, ESPECIALLY KNEE JOINT

FIELD OF THE INVENTION

The present invention relates to a prosthetic device for a joint, and more particularly for a complex joint, and especially for the knee joint, having a first prosthetic part which contains an anchoring or attachment portion and at least one rotary joint portion, adapted to be secured to one of the bones which form the joint, for example the femur, and a second part which also contains attachment elements or stems, adapted to be attached to the shin bone or tibia, and formed with a sliding surface. An intermediate part or element is provided slidable between anterior and posterior directions and which, in association with a suitable section of the first portion, permits articulation of the joint.

BACKGROUND

Many solutions have been proposed for the problem of endoprosthetics, which permit unchangeable maintenance of a stable bone implantate joint, which will last for a very long time, ideally from implantation to the death of the patient or wearer of the prosthesis. There are, primarily, two factors which interfere with such lifetime implantation. For one, the interface between the bone-implantate is subject to changeable forces, which change both with respect to value as well as direction. Particularly shearing forces are involved. For another, biological reactions of tissues and degrading bones are a factor, especially reactions to foreign-body materials, and reactions to abraded particles from the prosthesis itself.

The long lifetime, and particularly implanted lifetime, of a joint can be increased by reducing changeable forces engaging at the interface between the various prosthetic parts, and on the sliding surfaces thereof. The wear on the sliding surfaces should be minimized. Various solutions have been proposed, but not all of them can be applied at the same time. It is not sufficient to consider all the technical aspects of the joint; anatomical as well as physiological changeable conditions must be considered. The complex kinematic which occurs in joints, and particularly in complex joints such as the knee joint, can make it difficult to compromise between conflicting solutions applicable to specific parts, to achieve the overall goal of lifetime reliability.

It is well known that the wear and tear on slide bearings can be reduced by decreasing the per-square or area pressure of the respectively rubbing sliding parts. The surface or area pressure, and the resulting wear and tear on the bearing, is small when the contact surface of the two sliding elements is large. This contact bearing surface can be increased by making the sliding surfaces as large as possible and effectively congruent. Typical examples for such bearings are shown in FIG. 1, in which a straight slide bearing is schematically illustrated, and in FIG. 2, which, schematically, illustrates a hinge or ball joint. The slide bearing of FIG. 1, in principle, can be considered as a hinge or ball joint in which the engaging surfaces have infinite radii. Yet, in spite of the common characteristic of minimal wear and tear, there are basic differences: The slide joint, FIG. 1, is free for translatory movement, but does not have an axis of rotation. The hinge or ball joint, on the other hand, has an axis of rotation, but is restrained from translatory movement. This results in different relationships with respect to externally acting forces.

Reference is again made to FIG. 1:

A force, such as force F1 coming from above at an inclination, results in lateral shifting of the sliding head due to horizontal component of the force. This horizontal component of the force does not have any effect on the lower part of the sliding joint.

A force similar to force F1, when applied to a hinge or ball joint, see FIG. 2, passes through the joint without causing any rotation thereof. The horizontal component of this force, however, results in an undesired shear force, which continuously changes its direction if the upper portion of the joint oscillates back and forth like a pendulum. Most simply, the hinge joint has the advantage of rotary movement, which, however, is obtained by accepting the disadvantage of translatory immobility, and shearing forces at the interface.

Human body joints rarely are pure hinge joints or pure slide joints. Usually, and especially the knee joint provides a combination of both. A rotary movement and translatory movement can be superimposed upon each other.

In order permit a combination of such movements, it is necessary to open the hinge joint, that is, it is necessary to reduce the congruence of the slide surfaces with respect to each other. Referring to FIG. 3, the contact surfaces are decreased which, however, substantially increases the area or surface pressure, and hence wear and tear on the joint. This wear and tear is further increased by repetitive translatory movement of the head of the joint on the slide surface. Due to the almost point or at best somewhat line contact, and hence a similar high surface pressure, a kneading process on the respective joint parts results which, in turn, causes material fatigue of the lower joint portion or component. The non-congruent position of the elements does not necessarily prevent the occurrence of shear forces at the interface. Raised slide surfaces at the interface result in forces which are similar to those which arise in a pure hinge or ball joint. The result is increased wear and tear as well as shear forces at the interface, which has undesirable effects in all prostheses of this type.

It has been proposed to use a combination of slide and ball joints, in which the sliding and ball joint components are located on two different planes, by using an intermediate element, see FIG. 4. The rotary movement of the ball joint and a translatory movement of the slide joint are vertically staggered, so that the translatory movement is available as a lower motion of the ball joint. The congruence of joint surfaces is fully retained; wear and tear is minimized. The forces supplied by the ball joint are not transferred to the interface but, rather, translated into translatory movement by the intermediate element. Prostheses are of this type are known, and have been referred to as meniscal knees.

U.S. Pat. No. 4,309,778, Buechel and Pappas, describes two different knee joint prostheses, which have also been referred to as the "Oxford Knee" and the "New Jersey Knee". The "Oxford Knee" has two femoral portions, two intermediate portions and two tibial portions. The femoral portions each have a spherical segment which has a retention section, for retention on the femur. The tibial parts also have retention on the tibia. The tibial parts not only have retention sections for attachment to the tibia, but also a flat plateau on which the intermediate part can slide.

Upon flexion of 90° and more, the intermediate part can slide over the flat or table-like surface and, possibly, can be entirely dislocated. A similar danger may occur if the tension of the remaining ligaments decreases after the operation and the femoral part lifts off the intermediate part. A new operation of the knee joint will then become necessary.

The "New Jersey Knee", described for example in FIG. 15 of the referenced U.S. Pat. No. 4,309,778, has a special arrangement to prevent loss of contact over the table or slide surface. Two dovetail-like, bowed grooves are provided on the tibia part; an engagement element is provided for the intermediate part element, fitting in the grooves through which the intermediate part element are constrained to be guided. The curves are directed towards the center, so that the intermediate part, upon bending of the knee, cannot slide backwardly in uncontrolled manner, and pushed over the surface or table, but, rather, engages the still remaining central projection from the bone. The dovetaile shape prevents dislocation or luxation of the joint, if the ligaments should lose tension or will have decreased tension or strength.

The intermediate portions are constrained to be guided on a predetermined path which permits congruence of the joint surfaces between the femoral portion and the intermediate portion only in a single position of the joint. For all other positions of the joint than the single one, an incongruence of joint surfaces results, which increases wear and tear of the engaging surfaces. Non-congruent conditions arise because the femoral parts, which are securely anchored in the femur, are always at the same distance from each other and have a common axis of rotation. The intermediate parts, however, approach each other laterally upon sliding forwardly and backwardly on the curved path or, respectively, separate from each other. Further, their axes of the hinge or ball joints continuously change their position with respect to each other. Similar situations obtain, in reverse sense, however, upon rotary movement about an axis which is perpendicular to the slide surface. The continuously changing degree of non-congruence of the surfaces of this prosthesis, and particularly of the hinge or ball joint surfaces, causes increased wear and tear and decreases the effect of a meniscal layer in a knee joint.

U.S. Pat. No. 4,353,136, Polyzoides et al, describes an endoprosthetic knee joint having a femoral, a tibial part and an intermediate part. The femoral part has an attachment portion for attachment to the femur and two condyles. The tibial part has an attachment portion and projecting attachment ribs for attachment to the tibia. The side opposite the attachment surface has a flat bearing surface, with a groove to receive a rib of an intermediate part. The rib of the intermediate part fits into the curved groove of the tibial part; two concave slide bearings provide counter surfaces for the condyles of the femoral part. This prosthesis has the advantage of congruence of the slide surfaces of a hinge or ball joint, and thus of low wear and tear.

The curved groove and rib coupling does not, however, permit translatory movement of the femoral part relative to the tibial part. It only permits rotation about the axis of the curve of the groove. This, then, is a classic hinge joint with additional freedom of rotation about an axis perpendicular to the hinge axis. Thus, forces which come at an inclination from above, see FIGS. 2-4, which occur, for example, due to muscle pull or loading upon placing the foot of the wearer on the ground, will pass through the joint to the interface and there result in the undesired shearing forces. The principle of a meniscal knee is compromised in that the congruence of the joint surfaces, which reduces wear and tear, is obtained only by loss of the translatory capability, which protects the connection between the prosthesis and the joint. The natural knee kinematics, thus, are not entirely obtained with this joint. Besides that, the use of elements which prevent dissociation or luxation of the joint, for example at dovetail interconnection, is nearly impossible, especially to permit insertion of the intermediate portion at a later time, after the tibial portion or part has already been implanted. This has the disadvantages which have been discussed above in connection with the "Oxford Knee".

British Patent 1,567,007, Minns et al, describes a knee joint having a femoral part, a tibial part and an intermediate part. The femoral part, as is customary, has an attachment element and a condyle. The tibial part also has an attachment element for connection to the tibia and a straight, dovetaile-shaped groove to receive a matching rib of the intermediate part. The intermediate part has a straight rib, fitting into the groove. The intermediate part, further, has a shallow glide bearing for articulation with the condyle of the femoral part. This structure also has the advantage of wear reducing congruence of the slide surfaces. The dovetail connection between rib and groove prevents luxation or dissocation of the intermediate part, and hence undesired separation from the tibial part.

This structure permits translatory movement in the longitudinal direction of the groove. It does not permit rotational movement about an axis perpendicular to the plane of the tibial part, that is, essentially perpendicularly to the axis of the tibia. Such rotary movements, however, are superimposed practically with all movements of the knee joint, which results in continuous non-congruent engagement of the slide surfaces of the condyle from the femur and the intermediate part. The natural kinematics or relative movements of the parts of the knee joint are thus not adequately reproduced.

THE INVENTION

It is an object to provide a prosthesis for replacement of injured or diseased joints, and particularly complex joints, and especially knee joints, which is so constructed that the components of the prosthesis are protected; that, when in use, they have low wear and tear, and which permit not only congruence of joint surfaces, translatory and rotary movement of a knee having an intermediate or meniscal portion, but also effectively ensures reliable retention of the intermediate portion with respect to dissociation or luxation. The joint should permit approximately normal physiological movement of the natural joint, which it replaces.

Briefly, the joint has an intermediate part which is guided with respect to another part, typically the tibial part, by a guide arrangement which includes a guide groove or guide track and a coupling portion operable in the guide track, and in which the guide track has a region in which it is widened beyond a fitting engagement with the coupling portion in order to permit the coupling portion freedom of movement with respect to the guide track—yet preventing removal of the coupling portion from the guide track.

The prosthetic joint in accordance with the present invention permits movement or articulation which largely corresponds to the normal physiological movement of a natural joint, typically a natural knee joint. Upon flexion, the condyles shift from ventral to dorsal; at the same time, however, a limited rotary movement can occur. In flexion as well as in extension, similar conditions obtain as in a natural knee. In any position of the joint, congruence of the joint surfaces between the femoral part and the intermediate part is assured, since the intermediate parts are not tightly guided but, rather, can move in the respective tracks, typically grooves, with lateral play. Thus, the joint surfaces on the intermediate parts can remain aligned with respect to each other. Forces transferred from above are not further transferred to the interface but, rather, are converted in the intermediate part in translatory movement. The danger of dislocation of the intermediate part, upon flexion, is effectively eliminated, since the motion or articulation of the joint corresponds largely to that of a normal physical motion of a natural knee.

The intermediate part can be a relatively small, exchangeable element. Thus, it is possible to fit, during the knee replacement operation, intermediate parts of suitable heights; sets with different heights can be provided. Such differently sized parts are suitable in order to compensate for flabbiness in ligaments or to correct axial misalignments. The intermediate part, as well as the femoral and tibial parts, can be made of different materials. For example, the intermediate part may be made of plastic and the parts of the prosthesis which are actually connected to the bones made of metal.

The coupling portion can be guided within the track portion, typically a groove, by suitable shaping of the side walls of the grooves. This results in a particularly simple construction. In order to be able to widen the groove, in anterior and posterior position, in accordance with the present invention, the directions and shapes of the groove can also be changed. Preferably, the side walls of the groove, in a region extending towards the edge of the tibial plate, for example, are curved. The groove can extend in a curve about a central axis. The coupling portion itself may also have a suitable curvature along its longitudinal extent. This permits rotation upon flexion as well as extension which is similar to movement in a natural joint. Preferably, the spacing between the side walls of the groove is smallest approximately in the center of the groove. The width of the coupling portion corresponds approximately to this minimum spacing.

In accordance with a particularly advantageous embodiment of the invention, the inner side wall of the groove is curved, whereas the outer side wall of the groove, particularly in the central region, has an essentially straight portion. The coupling portion, however, has the reverse situation in that the outer side wall of the coupling portion is curved and the inner side wall of the coupling portion, at least in the central region, has a straight portion. This permits maintenance of the lateral play between the guide portion of the intermediate element and the guide track to be small, so that the transverse stability of the knee will be high. This is particularly important for prostheses replacing a knee joint. The shape described provides both translatory movement in anterior/posterior direction and limited twisting movement of the intermediate part relative to the second or tibial part.

The radius of curvature of the outer side wall of the coupling portion or coupling element can be the same or smaller than the radius of a concentric circle about the inner side wall of the guide track, and which just is tangent to the straight section of the outer side wall of the guide track. The radius of this concentric circle can be about 1.3 to 2.6 times the radius of the curvature of the inner side wall of the guide track or guide groove. This dimensioning results in anterior and posterior widening of the guide track or guide groove, which provides the desired freedom of movement for the intermediate part, in its movement in anterior or posterior direction, respectively.

The curves need not be true circular curves; use of curves which are circular, however, has advantages from a manufacturing point of view. Other curves than circles can be used, for example elliptic curves.

Preferably, the movability of the intermediate part is constrained by a slide plane or guide plane, to inhibit wobble. To provide for positive guidance in a vertical direction, thus, the guide track or guide groove and the matching surfaces of the coupling portion, can be of dovetail interengaging connection, T-shaped, tongue and groove shaped, polygonal or circular cross section. Such shapes prevent loss of the coupling portion from the guide track if, due to some reasons, the retention of the ligaments of the joint decreases after the operation of joint reconstruction.

The rotary bearing surfaces can be constructed in different manner in order to ensure rotary movement. In accordance with a preferred feature of the invention, two condyles are provided, and each condyle is fitted on a suitable, matching bearing surface on the intermediate part. Preferably, the guide tracks or guide grooves are so arranged that they converge in anterior and posterior direction. The result will be a prosthesis in which the natural joint, for example in a knee joint, is closely approximated.

In accordance with a feature of the invention, two separate intermediate parts are used, one each being formed with the coupling portion and fitting in its own guide groove. In accordance with another feature of the invention, a bridge-like connecting part can be provided, coupling the individual intermediate parts together. Such connection prevents relative shifting of the intermediate parts with respect to each other, and a possible non-congruence of the rotary joint surfaces, in engagement with the condyles. The reliability with respect to dissociation or luxation, further, is improved, since the two coupled intermediate parts are imprisoned in the curved grooves, and cannot exit therefrom in anterior or posterior ends of the grooves. Further, the coupling provides a degree of damping, or braking of translatory movement when the end points or limits for movement are reached. This braking is particularly soft or gradual if, by suitable selection of the radii of curvature of the tracks and/or of the coupling portions, the concave inner surfaces of the coupling portions can first engage with the convex side walls of the groove.

Forming the coupling element as a cross-connecting bridge has the advantage that, if the intermediate parts are made of plastic, cold-flowing of the plastic material, and hence another factor which leads to material fatigue, and hence wear, is excluded.

The construction of the joint can be formed in a mono-compartmental manner, that is, the joint portion of the first prosthesis element can be formed by a single condyle, and the matching receiving surface on a single intermediate part of sufficient size to be able to accept the single condyle.

Preferably, and as an analog to a natural joint, the condyle is formed on the first prosthesis part and convex; the matching bearing surface of the intermediate part is then concave. It is also possible, however, to reverse this arrangement, where it is suggested by the anatomic structure, and to form the condyle on the intermediate part with the concave reception surface on the first prosthesis.

The prosthesis is particularly suitable for knee joint replacement. In such a case, the second or tibial part can be formed with a suitable recess for the anterior and/or posterior cruciate ligament. The prosthesis can readily be shaped to provide such a recess or room for these ligaments, which has the advantage that the important function of the cruciate ligaments for proper knee movement is retained.

The free path length of movement upon translation depends essentially on half of the difference in width between the guide track portion or guide groove portion and the coupling portion, as well as the radii of the concave side walls of the groove portion and the coupling portion, respectively. There is a positive correlation, that means, the free path length increases at increasing difference in width and/or absolute size of the radii.

As an example, the translatory extent of the guide track is assumed to be 15 mm. The radius of the outer side wall of a guide track portion in form of a groove is selected at 50 mm. This is suitable for a knee joint. The width difference then can be 1.13 mm. In a free translatory movement path of 25 mm, and a radius of 70 mm—which is rather high—the width difference may be 2.25 mm. In both cases, thus, the lateral play or freedom is within the limits of tolerances, which are normal for a stable knee joint. The lateral play or gap of the coupling portion in the guide groove, at the narrowest point, preferably is in the range of between 0.5 to 3 mm.

In accordance with a suitable embodiment of the invention, the radius of curvature of the outer side wall of the groove is approximately 3 times the radius of curvature of the inner side wall. This dimensioning results, directly, in anterior and posterior expansion or widening of the guide track, which then will result in the desired freedom of movement for the coupling portion and hence the intermediate part in its movement between anterior and posterior direction. The radius of curvature of the outer side wall of the coupling portion is, preferably, about half the radius of curvature of the outer side wall of the groove. The curves may be elliptical or have other shapes; a circular curve is preferred, however, since it is the easiest to fabricate.

DRAWINGS

FIG. 5 is a top view, partly in section, taken along line V—V of FIG. 6 of a knee joint prosthesis, in which, for ease of illustration, the outlines of the intermediate parts are shown in chain-dotted configuration;

FIG. 6 is a section along line VI—VI of FIG. 5;

FIG. 13B illustrates the joint of FIG. 13A in exploded view;

FIG. 13C is an upside-down detail view of an intermediate part;

DETAILED DESCRIPTION

Figure 1:
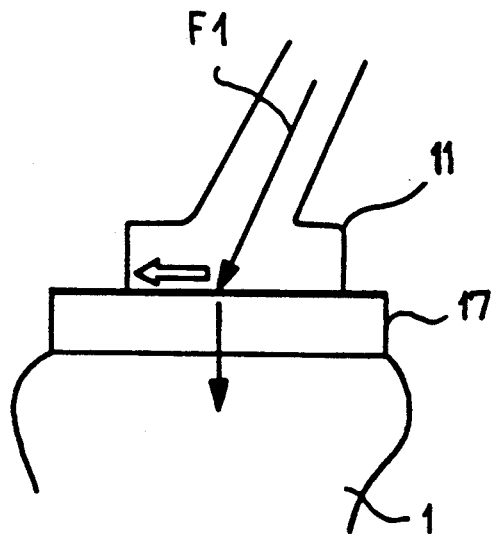
FIG. 1 is a highly schematic diagram illustrating force relationships in a sliding joint, and causing translatory movement.
Figure 2:
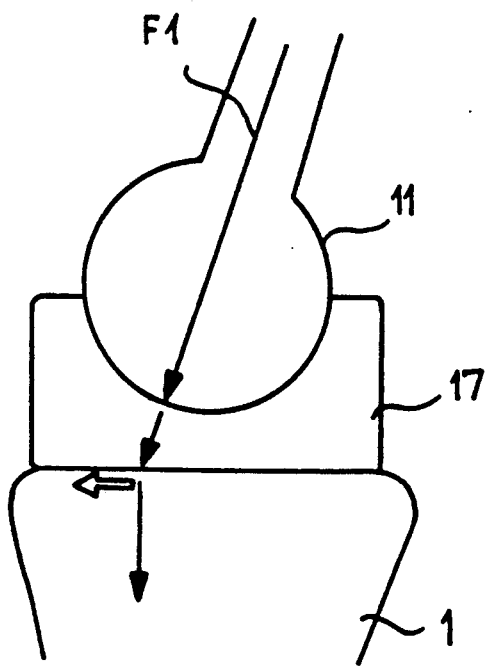
FIG. 2 is a highly schematic diagram showing shear forces which arise in a ball joint.
Figure 3:
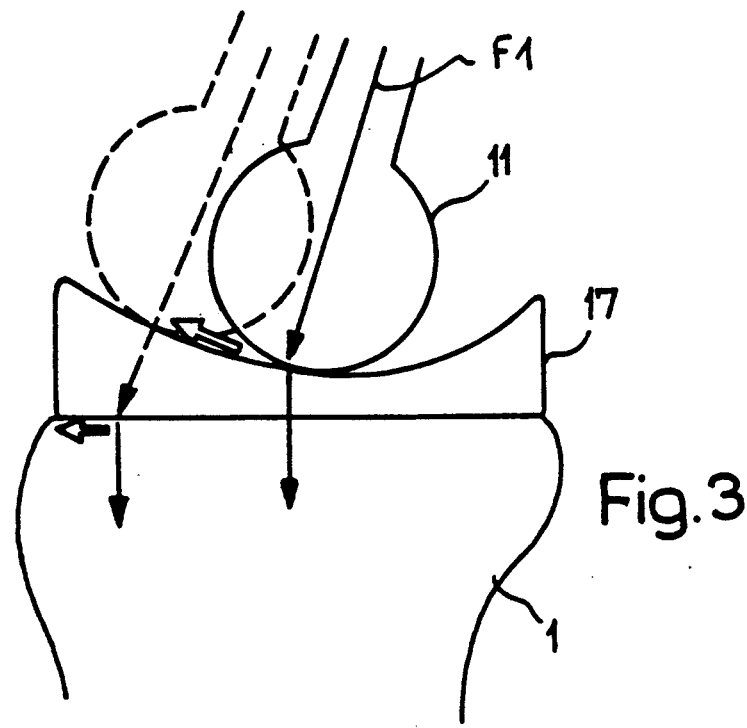
FIG. 3 is a highly schematic diagram illustrating forces which arise in an "open" ball joint.
Figure 4:
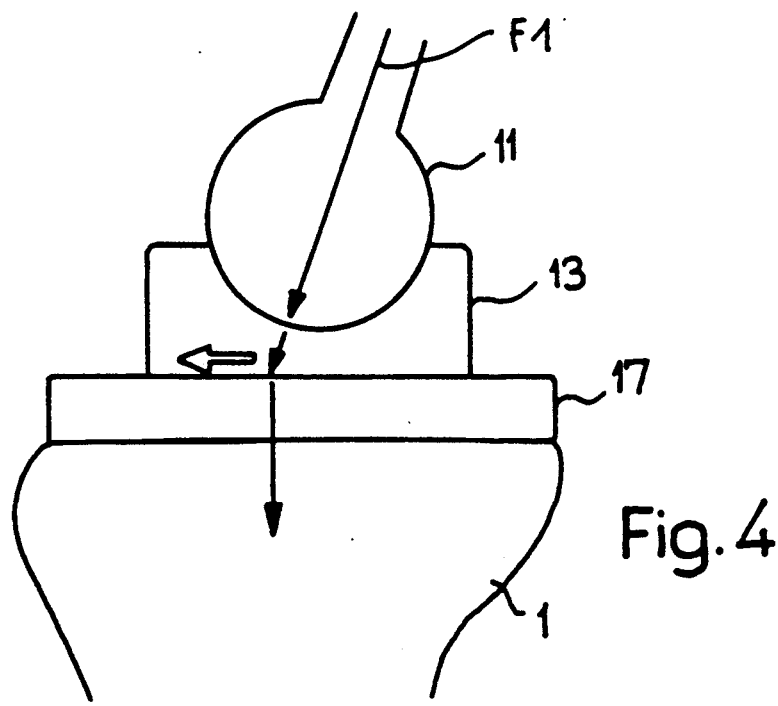
FIG. 4 illustrates the force relationships in a composite slide-ball joint.

FIGS. 1–4 show, highly schematically, the force relationships and force transfer conditions when a force F1 is applied by, for example, the femur or a femoral part 11 to a tibial part 17, secured for example to the tibia 1. FIG. 3 in addition shows the intermediate or meniscal element 17. In the actual joint, the element 11 is secured to the femur, not shown.

Figure 6A:
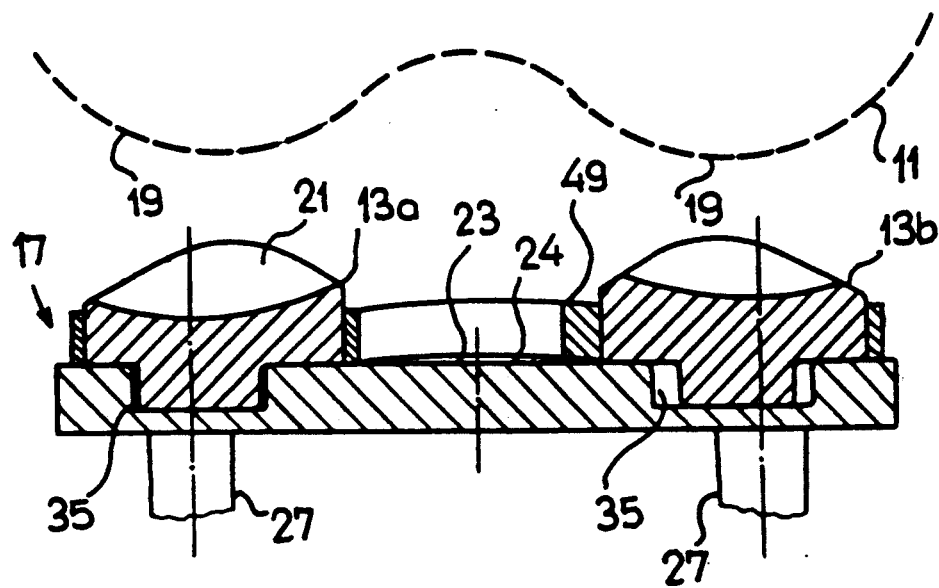
FIG. 6A is a section line through the embodiment of FIG. 5A.
Figure 6B:
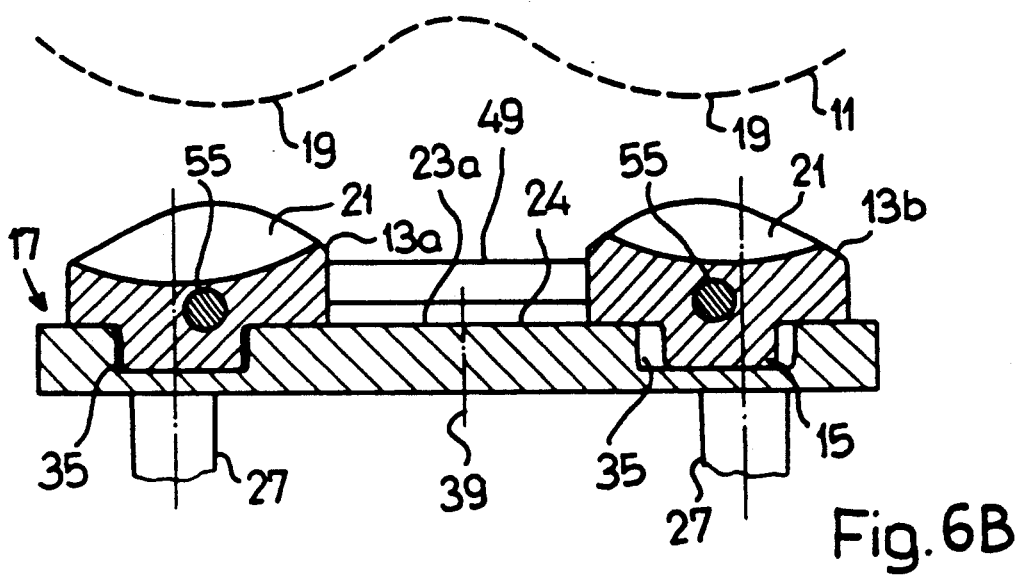
FIG. 6B is a section along line VIB—VIB of FIG. 5B.
Figure 6C:
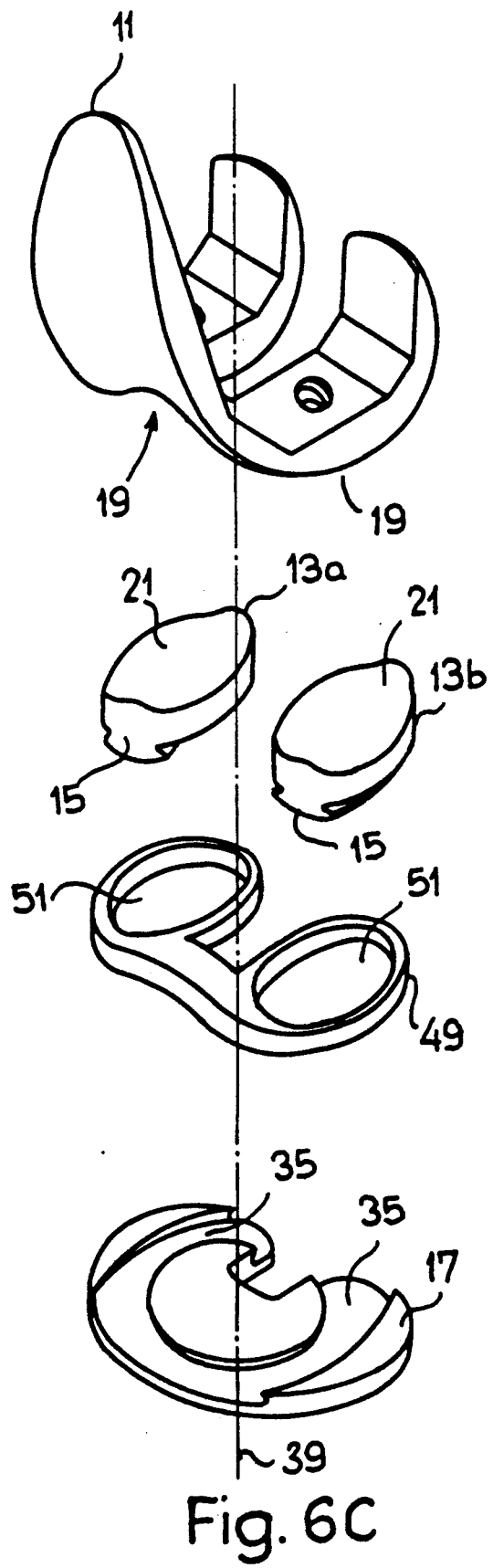
FIG. 6C illustrates a joint similar to the joint of FIG. 6A in exploded view.

Referring next to FIGS. 5 through 8:

As best seen in FIG. 6, the prosthesis has a first prosthesis part 11. This part is typically attached to the femur by a suitable attachment element shown schematically only at 11a, and hence may be referred to as a femoral part. The prosthesis further includes a second part 17, having attachment elements 27, for attachment to the tibia, which may also be referred to as a tibial part. In addition, the prosthesis has a two-element intermediate part 13, in which the intermediate part elements are designated 13a, 13b, respectively.

The first prosthesis part 11, besides the attachment portion 11a, is formed with a rotary joint portion 19. This rotary joint portion 19, as seen in FIG. 6, is formed by two condyles 19. The intermediate part elements 13a, 13b each have matching bearing surfaces 21, having radii of curvature which fit the curvature of the condyles 19.

Figure 5A:
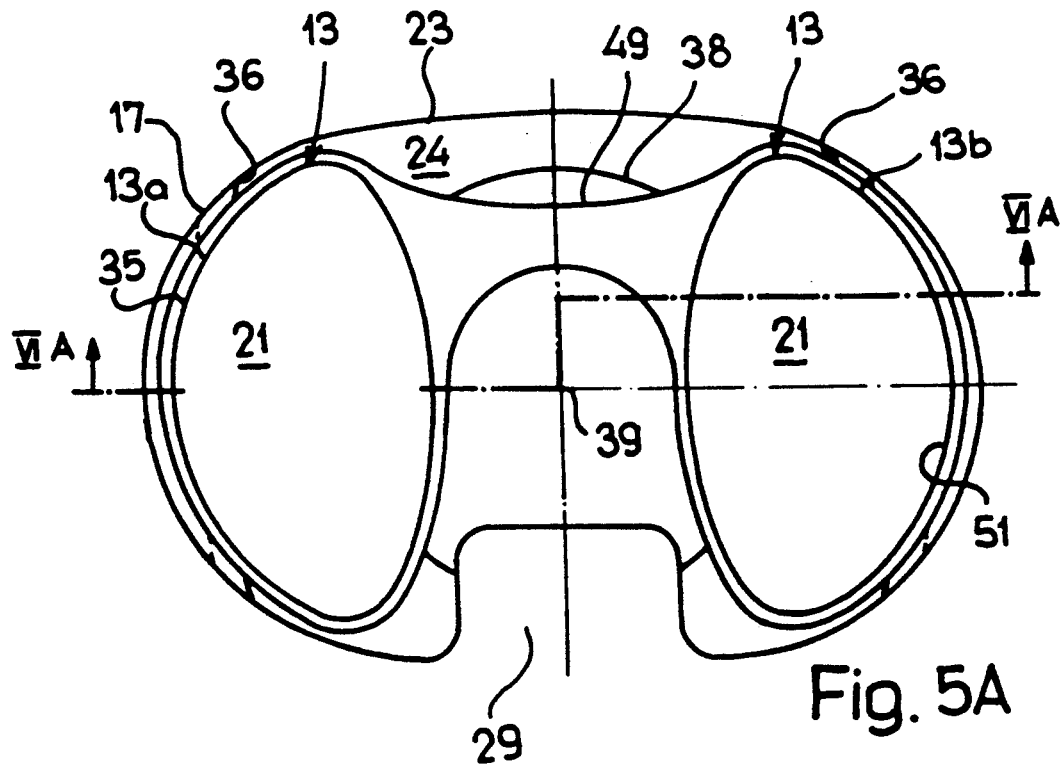
FIG. 5A is a top view of another embodiment.
Figure 7:
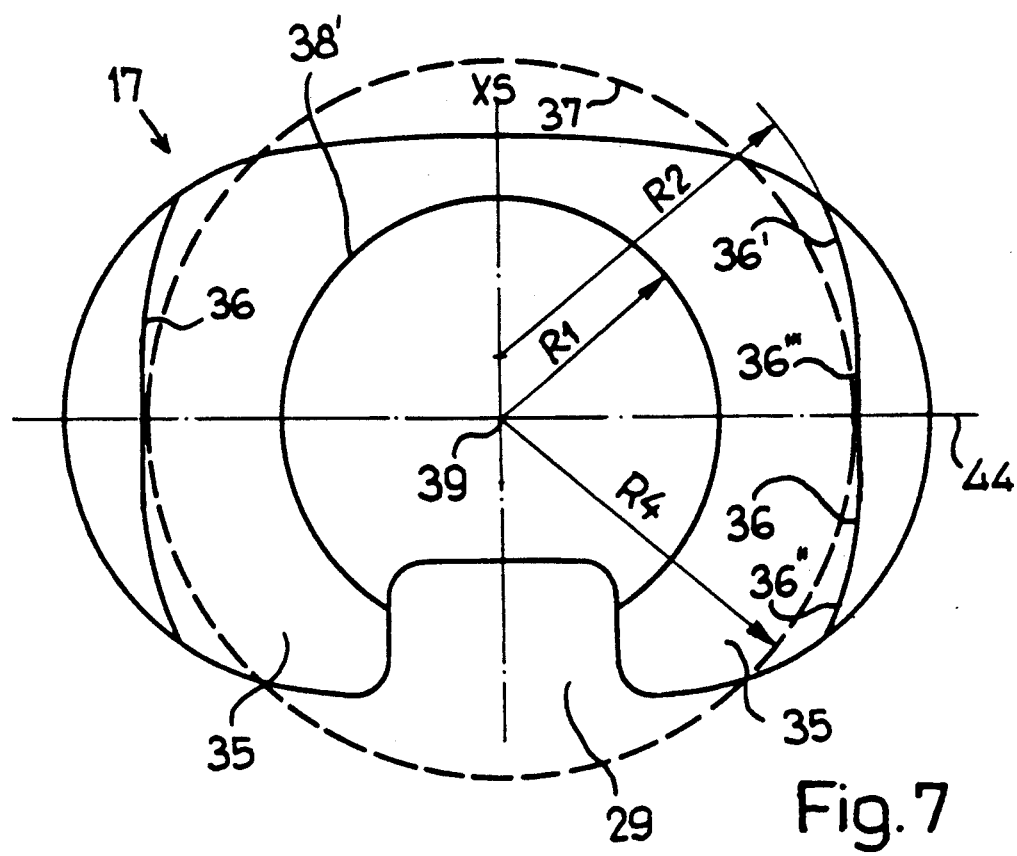
FIG. 7 is a schematic top view of the second prosthesis part of either FIGS. 6, 6A or 6B, omitting the intermediate parts.

The second prosthesis part 17 has a plate 23 from which the attachment parts 27 project. These attachment parts 27 may be conical, fins, posts or of other suitable construction. The plate 23, on its top surface, has a slide surface 24. As best seen in FIGS. 5 and 7, plate 23 is essentially oval, matching approximately the outline of a natural end portion of the tibia, formed with a posterior recess 29 to accept the posterior cruciate ligament. In accordance with an advantageous feature of the present invention, the recess 29 can be made so deep that it also can accept the anterior cruciate ligament, as illustrated, for example, in FIG. 12.

The second prosthesis part 17 includes two guide tracks 35. The guide tracks 35 are in form of grooves, which may have dovetail, T, or tongue-and-groove side walls, or any other suitable cross section.

In accordance with a feature of the invention, each groove 35 is laterally expanded towards the anterior and posterior end portions, as best seen in FIG. 5. The side walls 38 of the grooves are curved. The side walls 36 have curvatures 36', 36" at the anterior and posterior regions, respectively. In the central portion, they have an essentially straight region 36'''. The smallest distance between the inner side wall 38 and the outer side wall 36 is in the center region of the guide grooves.

Figure 8:
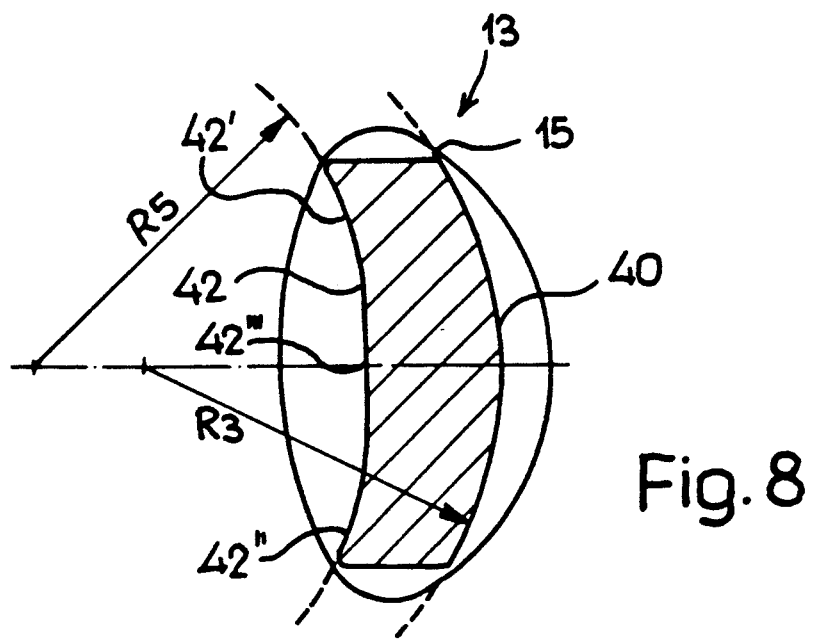
FIG. 8 is a bottom view of an intermediate part.

The shape of the intermediate parts 13 is best seen in FIGS. 5, 6 and 8. The condylar bearing surface 21 for the condyles 19 is formed on one side and in an upper portion 13a', 13b' of the intermediate part element 13a, 13b. The lower portion of the elements 13a, 13b has, projecting from the lower side, a projecting coupling portion in form of a guide extension or rib 15. The guide extension or rib or coupling portion 15 is elongated—see FIG. 5—and slightly curved. The inner side wall 42 of the guide portion 15 has anterior and posterior curved regions 42', 42", respectively, and an essentially straight region 42''' in essentially the middle of the elongated guide portion 15.

The radius R3, see FIGS. 5 and 8, of the outer side wall 40 of the guide element 15 is approximately the same, or smaller than the radius R4 of the theoretical circle 37. Circle 37 is concentric with a circle 38' of radius R1 defining the inner side wall 38 (FIG. 5) of the guide groove portion 35. The circle 37 is tangent to and just touches the straight portions 36''' of the outer side wall 36 of groove 35. It is about 1.3 to 2.6 times greater than the radius of curvature R1 of the inner side wall 38. The radius R3 of outer wall 40 of the guide portion 15, see FIGS. 5 and 8, can be somewhat smaller than radius R4, for example if the outer side wall 40 is elliptical. The radius of curvature R2 of the outer side wall 36 of the groove 35 is about equal to or slightly greater than the radius R3 of the outer side wall 40 of the guide projection 15. The center point of the circle with radius R2 is shifted along an axis XS. Thus, the portion 36', 36" of the wall 36 in the anterior and posterior regions will be further from the center 39, resulting in a widened groove 35. It is also possible, however, to make the radii of curvature 36', 36" larger, i.e. the curvature somewhat more flat.

FIG. 8 also shows radius R5 of the end regions 42', 42" of the inner wall 42, which is approximately the same, or somewhat greater than the radius R1 of the inner side wall 38 (FIG. 7).

The shape of the side walls of the guide track portion or guide groove 35 as well as of the coupling or projecting portion 15 which, together, form a coupling means between the intermediate part 13 and the tibial part 17, permit lateral play to be small. Expressed in other words, the intermediate part elements 13a, 13b can be shifted in the direction of the axis 44 (FIG. 5), but only to a very limited extent. Thus, the joint has a high transverse stability, without, however, preventing limited twisting movement.

Figure 10B:
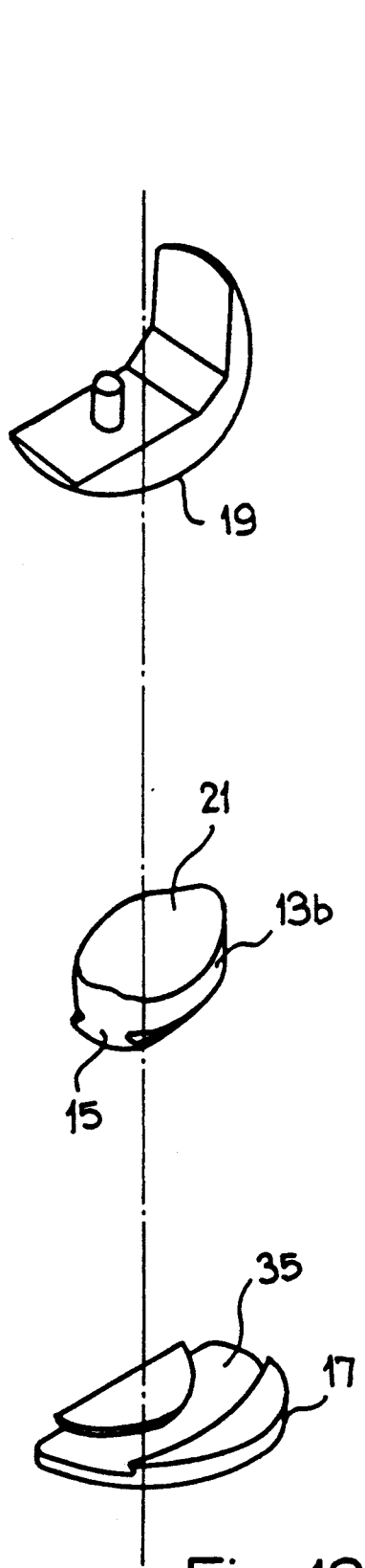
FIG. 10B illustrates the joint of FIG. 10A in exploded view.
Figure 10A:
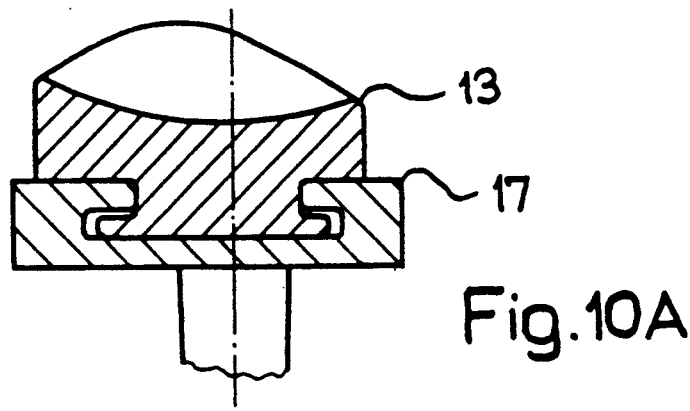
FIG. 10A is a section along line X—X of FIG. 9.
Figure 11:
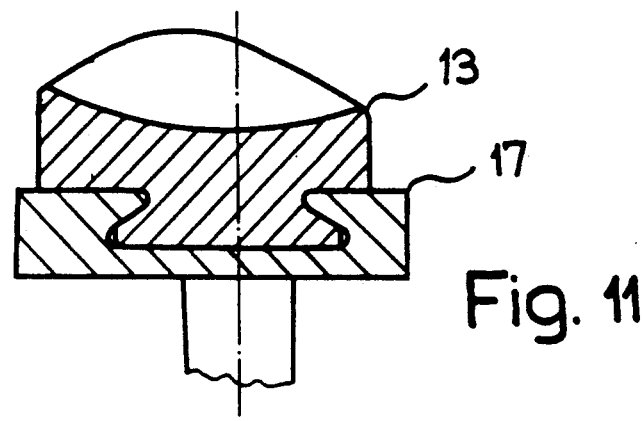
FIG. 11 illustrates another shape of a guide track arrangement, different from that of FIG. 1.

FIGS. 5 and 6 illustrate the basic structure, and the coupling portion 15 as well as the guide grooves 35, in vertical cross section; they are shown as essentially rectangular. As best seen in FIGS. 10 and 11, the cross section of the coupling portion can be differently shaped, for example tongue-and-groove, or T-shaped (see FIG. 10), or dovetail-shaped (FIG. 11). The particular shapes shown in FIGS. 10 and 11 limit the movement of the intermediate part elements 13 for sliding on the flat surface 24 of the plate 23, and hence in the plane of the surface 24.

Comparing FIGS. 5 and 6, one can see that the effectively mirror-symmetrical arrangement about axis XS of the coupling means formed by the guide portion 15 and the guide track 35 permits rotation about the axis 39, as well as translatory movement from anterior to posterior, and reverse, while retaining the congruence of engagement between the condyles 19 and the bearing surface 21 of the intermediate part elements 13a, 13b. The rotary as well as translatory movement is guided, after installation of the prosthesis in the body of the user, by the ligaments of the knee joint. The movement of the knee joint upon flexion and extension corresponds essentially to the physiological movement of a natural knee joint.

The guide track 35 as well as the coupling portion 15, in the arrangement shown in the figures, permits rotation about the axis 39 without, however, interfering with the congruence of the condyles 19 on the surfaces 21

Preferably, the first and second prosthesis parts 11, 17 are made of a metal alloy, as is usual for prosthetic joints. The intermediate part elements 13, preferably, are made of plastic material, of a composition which is also customary in joint prostheses.

The embodiment illustrated in FIGS. 5 and 6 shows two pairs of condyles 19, 21 in engagement. It is also possible to use only a single condyle-bearing combination. Other jointed connections, for example a hinge joint coupled by a hinge point, could be used, in combination with a suitable change of the intermediate part 13 and the part elements 13a, 13b, as well as of the coupling portion 15.

EMBODIMENT OF FIGS. 5A, 6A, 6C

The basic structure is similar to the prosthesis shown in FIGS. 5 and 6. In addition to the elements shown therein, a connecting portion or element 49 is provided, which rigidly couples together the intermediate part elements 13a, 13b. The connecting portion 49 located between the part elements 13a, 13b prevents relative movement between these parts, and thus possible non-congruence between the condyles 19 and the bearing surfaces 21. As described above, the connecting portion 49 also increases the reliability with respect to luxation or dissociation. The connecting part 49 is a somewhat eyeglass-shaped structure. Preferably, it is made of metal or a fiber-reinforced plastic. The openings 51 of the coupling element 49, which surround the intermediate part elements 13a, 13b, are matched to the contour of the intermediate part elements 13a, 13b. The connecting element 49, thus, after fitting the intermediate part elements 13a, 13b in the respective guide tracks, can merely be slipped over the intermediate part elements.

EMBODIMENT OF FIGS. 5B, 6B

Figure 5B:
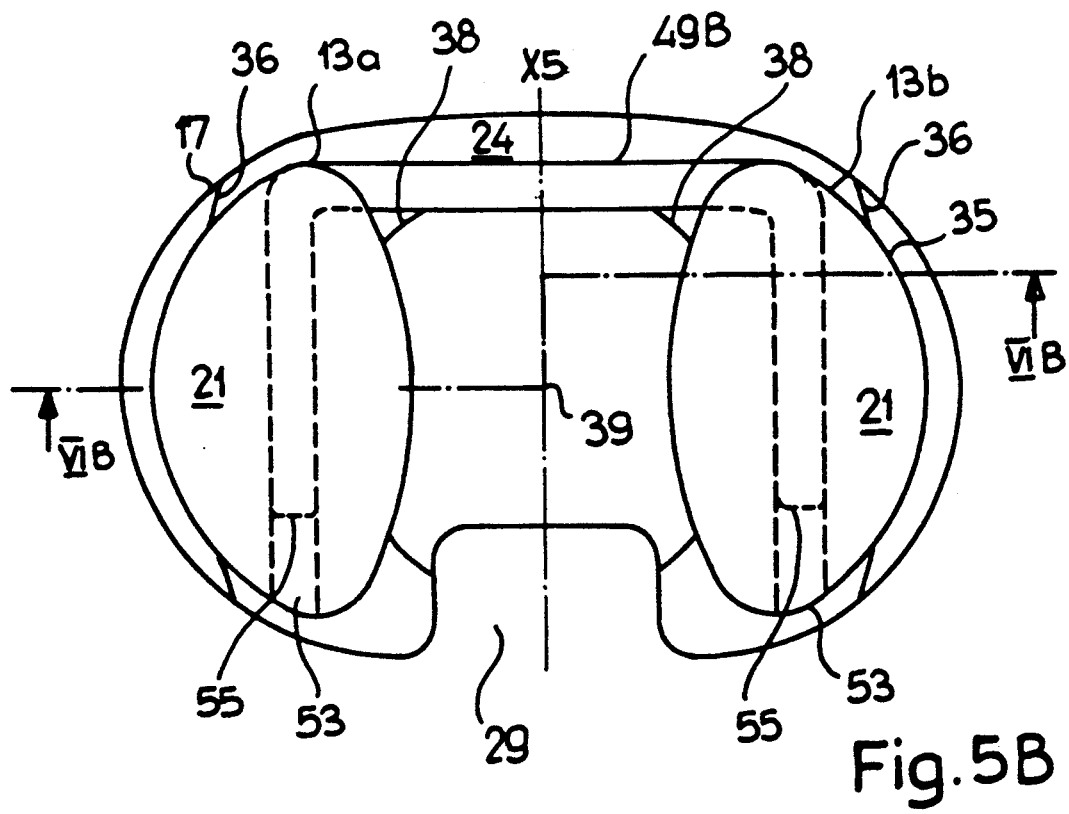
FIG. 5B is a top view of another embodiment showing a bridge connection of two intermediate part elements.

FIGS. 5B, 6B illustrate another way of coupling the intermediate part elements 13a, 13b. A U-shaped connecting bracket or clip 49B is inserted in suitable bores 53 formed in the intermediate part elements 13a, 13b. These bores 53 receive the legs 55 of the generally U-shaped clip 49B. The clip 49 can be inserted after placing the intermediate part elements 13a, 13b in position. The clip 49B can be made of metal.

In the embodiment of FIGS. 6, 6A and 6B, condyles 19 of the first part 11 are convex and the bearing surfaces 21 of the intermediate part 13 are concave. This corresponds to the natural joint. It is also possible, where it is suggested by the shape of the joint, rather than forming the condyles 19 on the first prosthesis part and concave bearing surfaces on the intermediate part, to form projecting condyles on the intermediate part, and respective concave bearing surfaces on the first prosthesis part 11, see FIG. 17.

EMBODIMENT OF FIGS. 9, 10A AND 10B

In general, the prosthesis corresponds to a half-portion of the prosthesis shown in FIG. 5. This is a monocompartmental prosthesis, to accept one condyle from the femoral part to provide a single bearing surface on the tibial part. FIGS. 10 and 11, additionally, illustrate guide surfaces. The reference numerals are the same as those previously described.

EMBODIMENT OF FIGS. 12, 13A, 13B, 13C

The position of guide track portion and coupling portion of the coupling means can be reversed with respect to the intermediate part 13 and the tibial part 17. Thus, the guide tracks 1235a, 1235b can be formed in the respective intermediate part elements 1213a, 1213b, and the coupling portion 1215a, 1215b formed as a projection from the plate 1223 of the tibial or second part 17. In all other respects, and specifically with respect to the various radial arrangements, the embodiments are similar to those described with respect to FIGS. 5 and 6. Of course, interlocking couplings for the coupling arrangement 1215a, 1235a, 1215b, 1235b, such as dovetails, tongue and groove connections and the like, may also be used, as illustrated in detail in FIGS. 10A and 11.

EMBODIMENT OF FIGS. 14 AND 15

Figure 15:
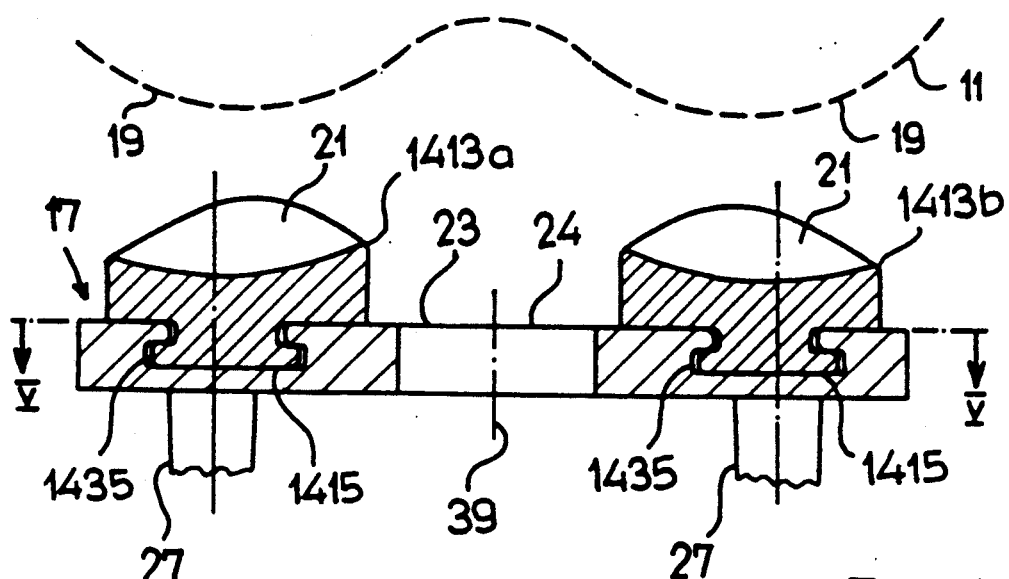
FIG. 15 is a cross-sectional view taken along line XV—XV of FIG. 14.
Figure 14:
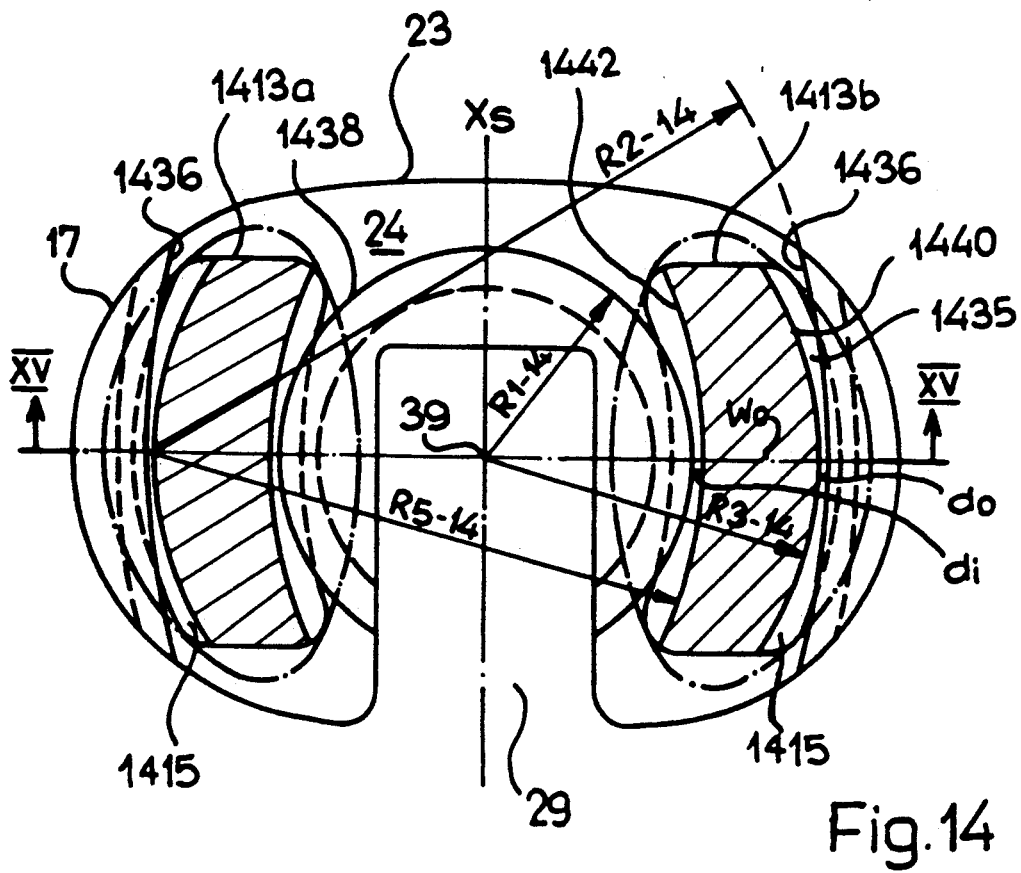
FIG. 14 is a view similar to FIG. 5 and illustrating a different arrangement of radii of curvature for the respective components of the knee.

The general arrangement of the prosthesis is similar to that described in connection with FIGS. 5 and 6, and like elements have been given similar reference numerals, incremented by the number of figures on which they first appear. FIGS. 14 and 15 also illustrate the interengaged coupling of the intermediate part elements 1413a, 1413b as described above in connection with FIG. 10.

In accordance with another feature of the invention, the radius of curvature R2-14 of the outer side wall 1436 of the guide track 1435 is about three times as great as the radius R1-14 of the inner side wall 1438 of the track 1435.

In accordance with another feature of the invention, the radius of curvature R3-14 of the outer side wall 1440 of the guide portion 1415 of the intermediate part elements 1413a, 1413b is smaller than the radius R5-14 of the inner side wall 1442 of the guide portion 1415. Therefore, the guide portion 1415 has its largest width Wo approximately at its middle.

FIG. 14 also illustrates that the clearance between the coupling portion 1415 and the guide track portion 1435, overall, is small. The inner clearance di and the outer clearance do, together, should preferably be between about 0.5 to 3 mm at the narrowest region of the guide track portion 1435, that is, where the guide track and the coupling portion 1415 are closest together.

Preferably, the radius R3-14 of the outer side wall 1440 of the guide portion 1415 calculates as the sum of the radius R1-14 of the inner side wall 1438 of the guide track 1435 plus the inner clearance di plus the largest width Wo, whereas the radius R5-14 of the inner side wall 1442 of the guide portion 1415 calculates as the difference of the radius R2-14 of the outer side wall 1436 of the guide track 1435 minus the outer clearance do minus the width Wo.

FIG. 14 also illustrates the deep recess 29 which permits acceptance of both the anterior as well as the posterior cruciate ligaments. The arrangement is mirror-symmetrical about the axis of symmetry XS.

Figure 9:
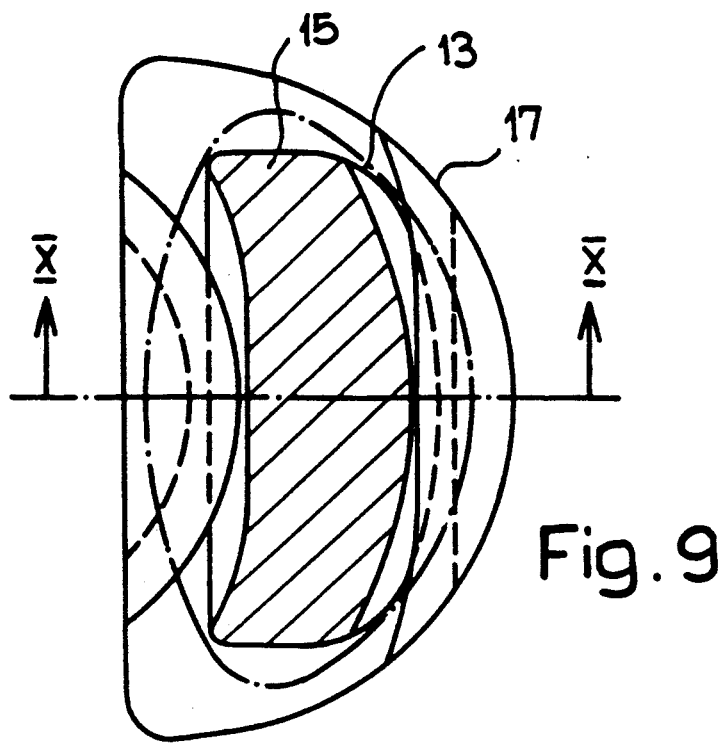
FIG. 9 is a top view of another embodiment of a knee joint prosthesis.
Figure 17:
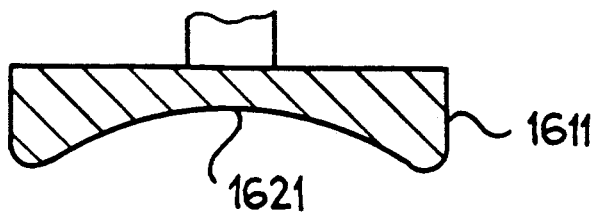
FIG. 17 is a cross section along line XVII—XVII of FIG. 16.
Figure 17:
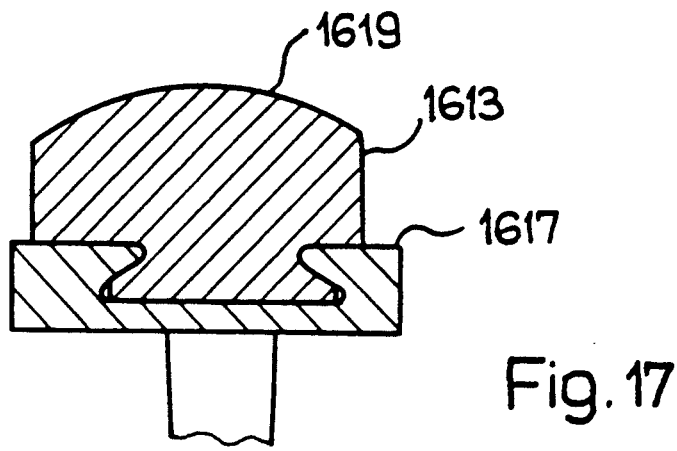
Figure 16:
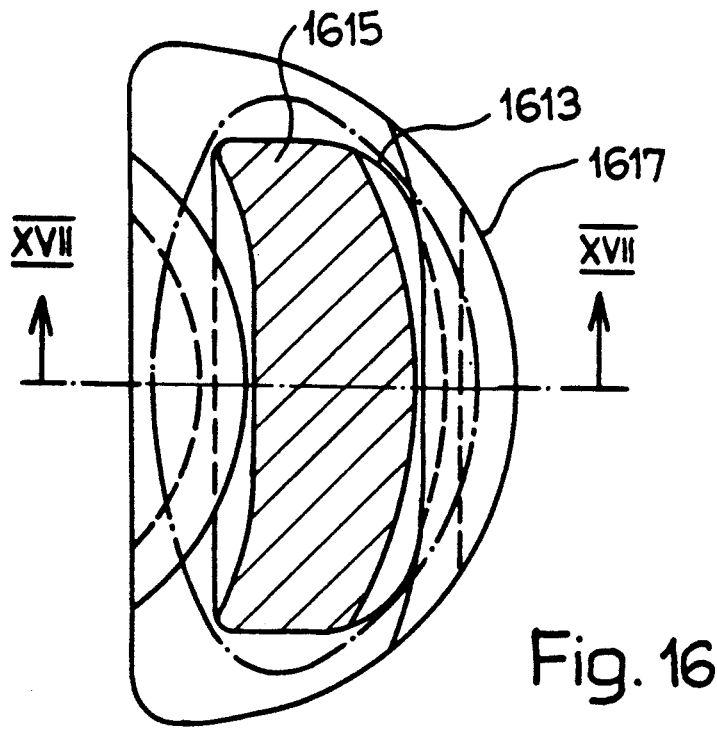
FIG. 16 is a top view of another embodiment with the femoral part removed.

FIGS. 16 and 17 illustrate an arrangement which is similar to that shown in FIGS. 9, 11, in which, however, the intermediate element 1613 is formed with a condyle 1619, and the first prosthesis part 1611 is formed with depressed cup-shaped bearing surfaces 1621, respectively.

Figure 19:
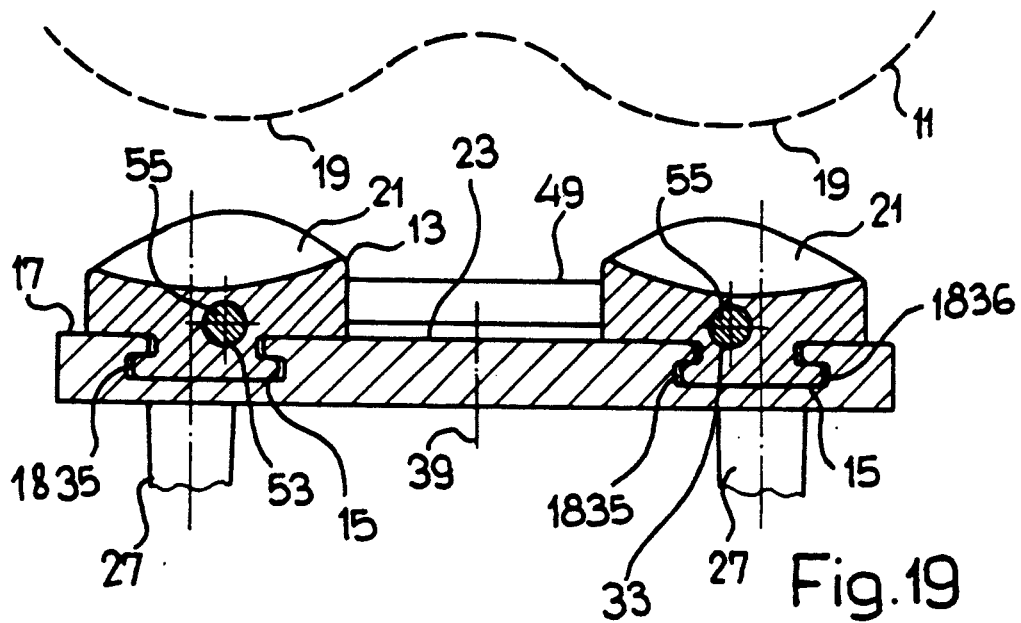
FIG. 19 is a cross section along line XIX—XIX of FIG. 18.
Figure 18:
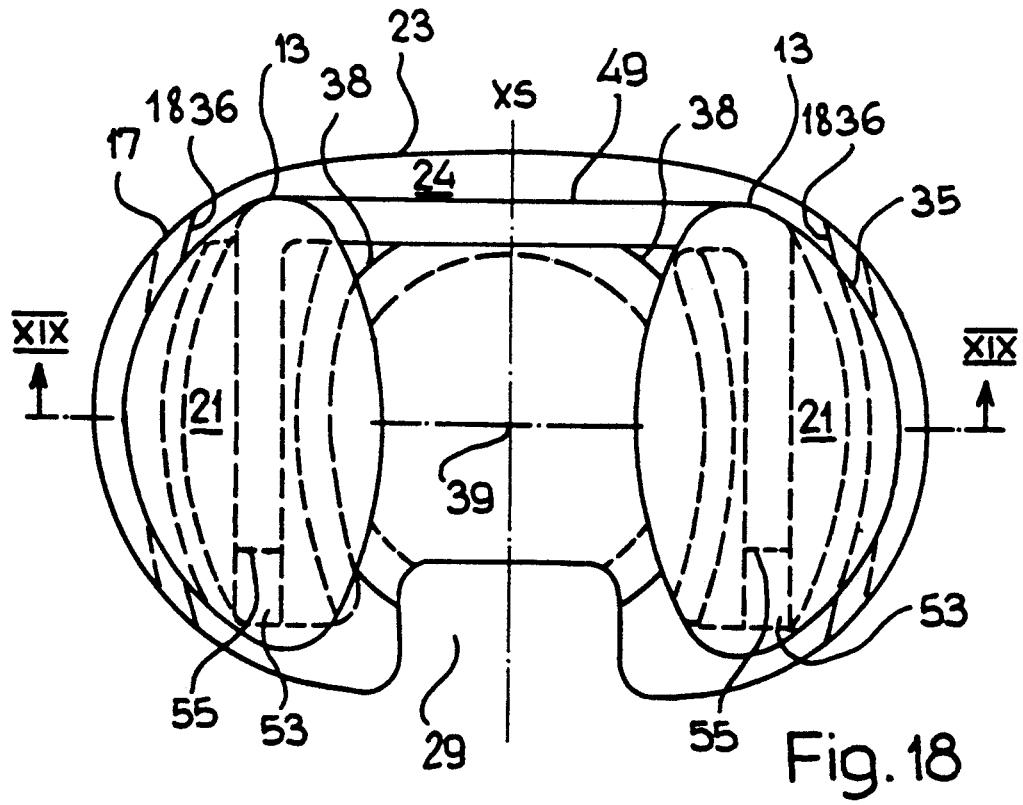
FIG. 18 is a top view illustrating yet another embodiment, with the femoral part removed.

FIGS. 18 and 19 illustrate an arrangement with a less curved outer surface 1836 of the guide track 1835, in accordance with the radius R2-14 (FIG. 14) which, in other respects, is similar to the embodiment previously described in connection with FIGS. 5B, 6B.

Figure 20:
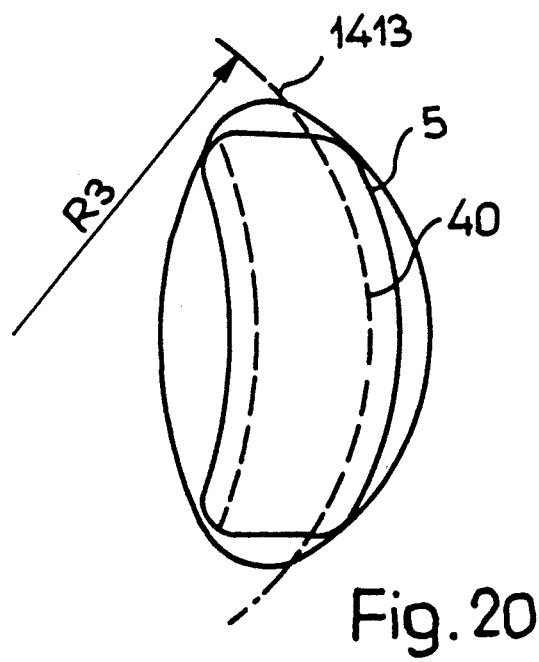
FIG. 20 is a bottom view of an intermediate part for a single-condyle femoral part.

FIG. 20 is a bottom view of an intermediate part element having an overlapping bottom surface, for example of the type illustrated in FIG. 10 or 11.

Figure 21:
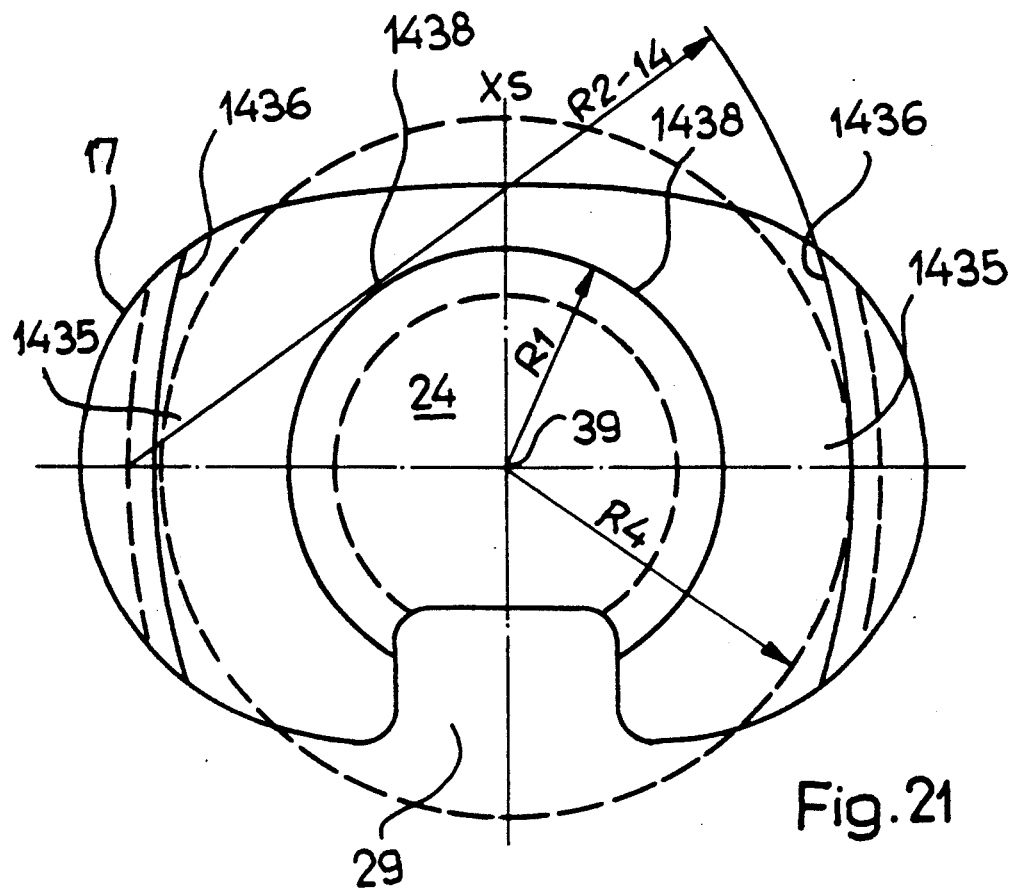
FIG. 21 is a top view of the second prosthesis part, with the intermediate parts removed.

FIG. 21 illustrates, highly schematically, the relationship of the respective radii of the tracks 1435, with the intermediate part elements removed, for ease of illustration.

Figure 22:
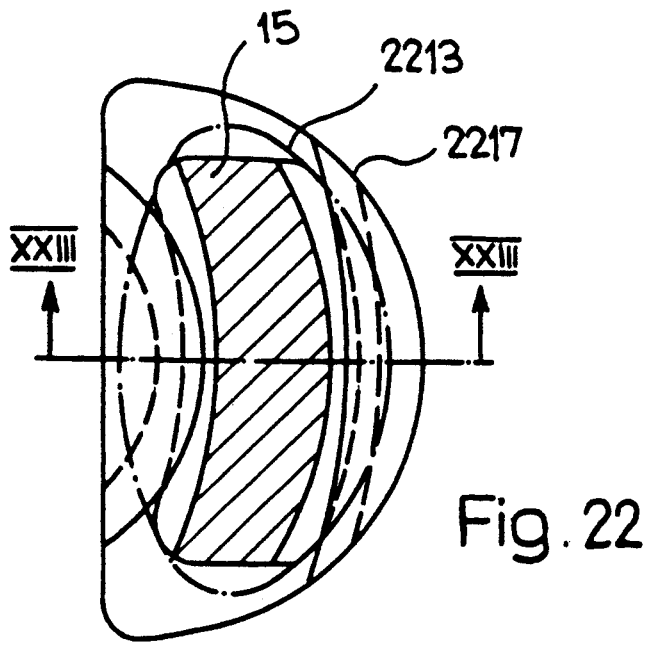
FIG. 22 illustrates another embodiment of a knee joint prosthesis.
Figure 23:
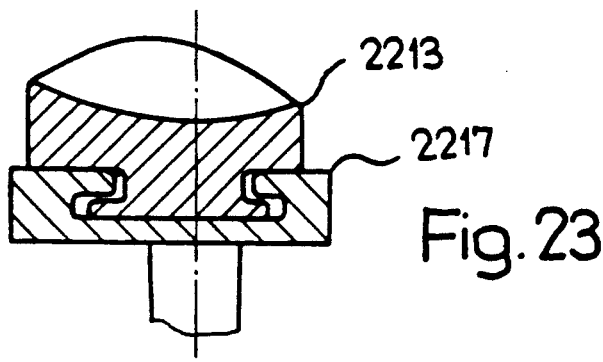
FIG. 23 is a section line along XXIII—XXIII of FIG. 22.
Figure 24:
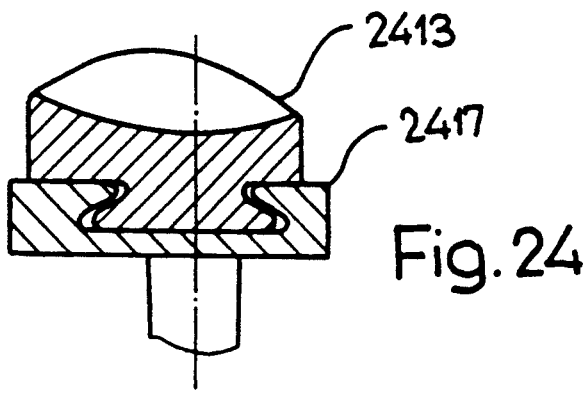
FIG. 24 illustrates an alternative embodiment of a guide track to that shown in FIG. 23.

FIG. 22 illustrates, in top view, a mono-compartmental prosthesis, similar to the bi-compartmental prosthesis of FIGS. 14 and 15, and FIG. 23 is a cross section taken along line XXIII—XXIII of FIG. 22. The single intermediate part element 2213 is seated on a slide surface of the second part 2217; the radii of curvature can be as described in connection with FIGS. 5 and 6, or FIGS. 14 and 21, respectively. FIG. 24 is another illustration of an interengagement of the guide track and coupling portion of the intermediate part 2413 with the second part 2417 in dovetail configuration.

Figure 13A:
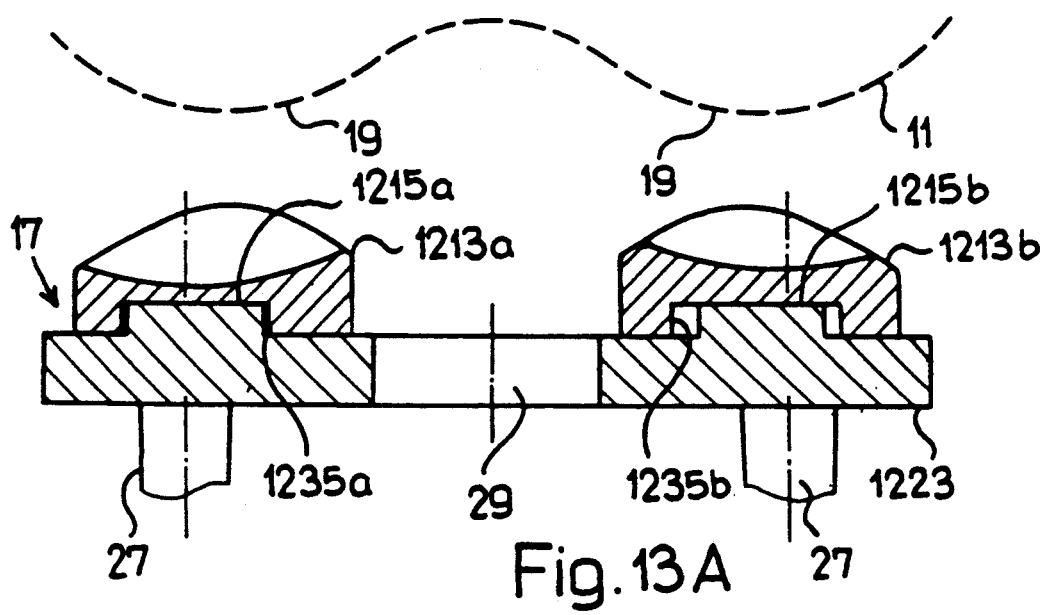
FIG. 13A is a cross section along line XIII—XIII of FIG. 12.
Figure 12:
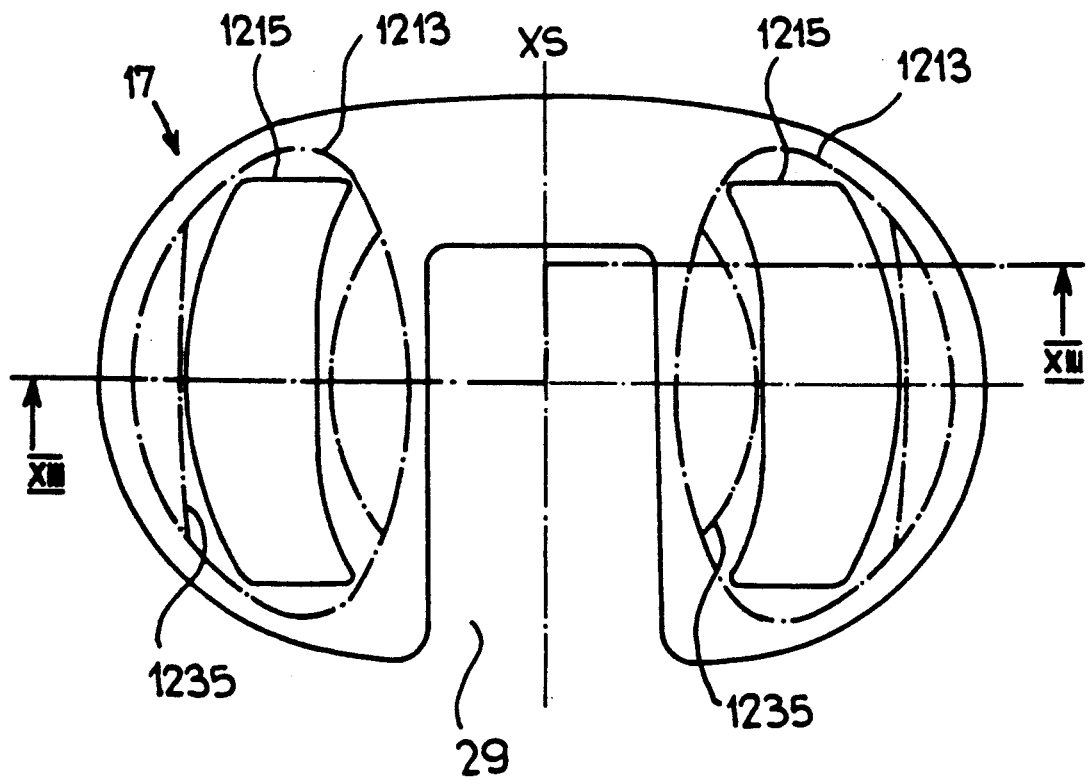
FIG. 12 is a knee joint prosthesis similar to that of FIG. 5, in which, however, the coupling portion is formed on the tibial or second prosthesis part.
Figure 26:
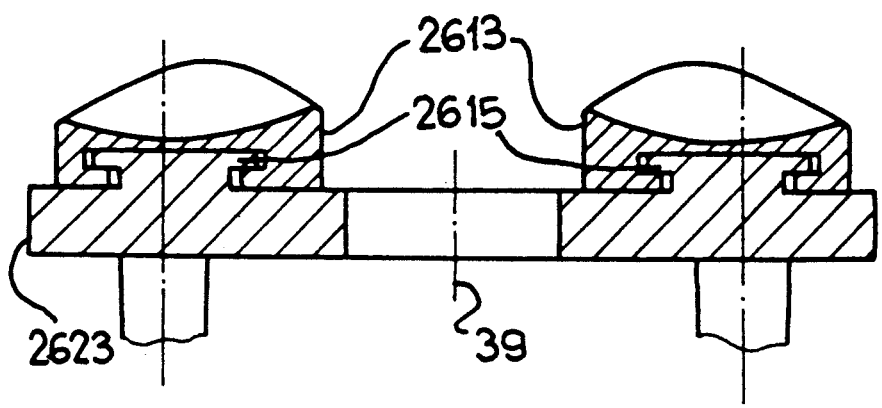
FIG. 26 is a cross section along line XXVI—XXVI of FIG. 25.
Figure 25:
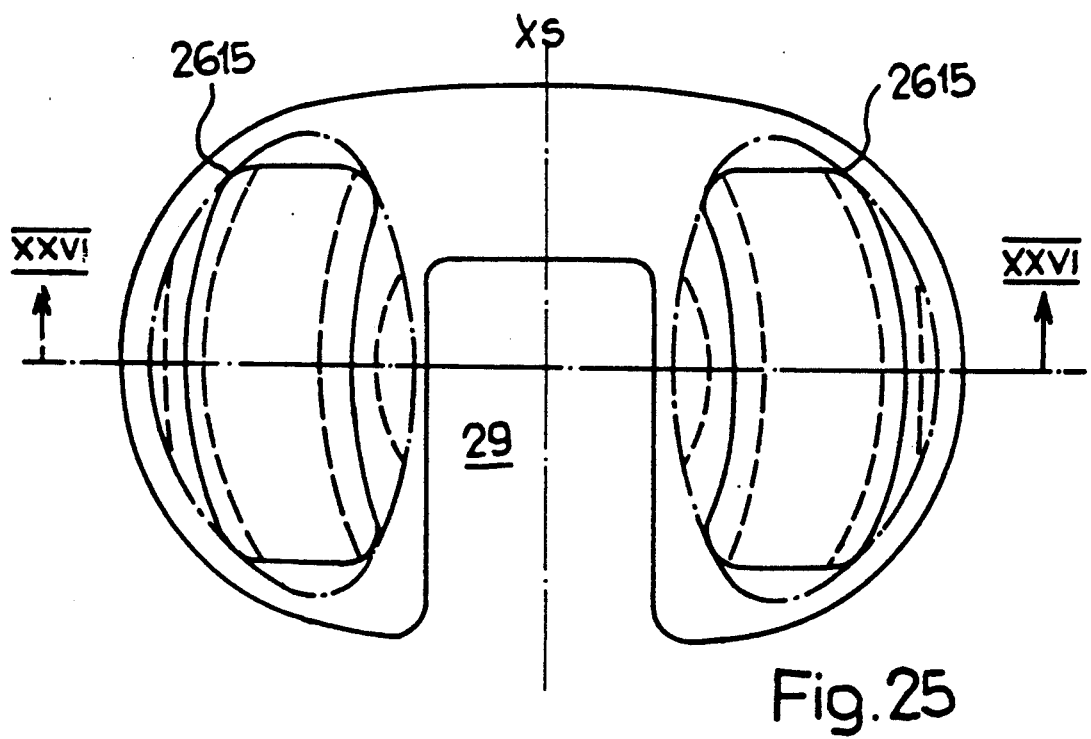
FIG. 25 illustrates a prosthesis similar to that shown in FIG. 18, in which the coupling portion is formed on the second prosthesis part.

FIGS. 25 and 26, respectively, illustrate arrangements similar to FIGS. 12 and 13 with, however, the curvatures shown in connection with FIGS. 14 and 21. The intermediate part elements 2613 are interlocked with the coupling portions 2615 by an overlapping T-connection projecting from the plate 2623. The position, thus, of the guide track with respect to the intermediate parts is reversed with respect to that of FIGS. 14 and 15. In all other respects, the joint is similar, and hence only those elements which differ from the ones already described have been specifically designated and discussed above.

Various changes and modifications may be made, and any features described herein may be used with any others, within the scope of the inventive concept.

I claim:

1. A prosthetic joint for replacement of a natural joint, especially a prosthesis for a knee joint, having
   a first prosthetic part (11, 1611) including a bone attachment portion (11a) and a condylar portion (19, 1621);
   a second prosthetic part (17, 23) formed with an essentially planar sliding surface (24) and including a bone attachment means (27, 1327);
   an intermediate part (13, 13a, 13b) located between said first and second prosthetic parts,
   said intermediate part including a bearing surface (21) on one side thereof shaped and dimensioned for cooperation with said condylar portion (19, 1621),
   first curved guide means (15, 1235a, 1235b, 1413a, 1413b, 1615) located on said intermediate part (13, 13a, 13b) at a side thereof opposite to said one side having said bearing surface (21);
   second curved guide means (35, 1215a, 1215b, 1435, 1835) located on said second prosthetic part (17, 23) at a side thereof facing said first guide means, and arranged for cooperation with said first guide means,
   one of said guide means comprising a groove extending in a substantially anterior-posterior direction and the other of said guide means comprising a projecting coupling portion located in said groove,
   said groove being formed with widened expanded regions, widening from a central region, both in anterior as well as posterior direction, to permit sliding movement as well as limited rotary movement of said projecting coupling portion within said groove.

2. The joint of claim 1, wherein (FIGS. 5-9, 14-24) the second guide track portion (35) comprises a groove (35) formed in the slide surface (23, 24) of the second prosthetic part (17).

3. The joint of claim 1, wherein said second guide track portion (35) is formed by a groove in one of:
   said second prosthetic part (17);
   said intermediate part (13), said groove defining an outer side wall (36) and an inner side wall (38).

4. The joint of claim 3, wherein both the outer and the inner side walls (36, 38) of the groove (35) are curved; and
   wherein the coupling portion (15) comprises an elongated projecting portion which is curved in its longitudinal direction.

5. The joint of claim 4,
   wherein the outer side wall (36) of the groove, in the central region, is essentially straight (36'''); and
   wherein the inner side wall (42) of the coupling portion (15) has an essentially straight region (42''') in a central region thereof.

6. The joint of claim 5, wherein the distance between the outer side wall (36) and the inner side wall (38) of the groove (35) is smallest in said central region; and
   wherein the width of the coupling portion (15) is just slightly smaller than said distance between the side walls (36, 38) of the groove in the central region.

7. The joint of claim 6, wherein the coupling portion (15) has an outer side wall (40) which is curved; and
   wherein the radius of curvature (R3) of the outer side wall (40) of the coupling portion (15) is equal to or less than a radius (R4) of a circle (37) concentric with a circle (38') defining the inner side wall (38) of the guide track portion (35), which circle (37) is tangent to the straight portion (36''') of the outer side wall (36) of the groove (35).

8. The joint of claim 7, wherein the radius of curvature (R4) of said concentric circle (37) is about 1.3 to 2.6 times greater than a radius of curvature (R1) of the inner side wall (38) of the guide track portion (35).

9. The joint of claim 6, wherein the difference between the width of the coupling portion (15) and the width of the guide track portion (35) of the narrowest region of the guide track portion is between about 0.5 to 3 mm.

10. The joint of claim 6, wherein the radius of curvature (R2) of the outer side wall (36) of the groove is about 3 times the dimension of the radius of curvature (R1) of the inner side wall (38).

11. The joint of claim 6, wherein the radius of curvature (R3) of the outer side wall (40) of the coupling portion (15) is about half the radius of curvature (R2) of the outer side wall (36) of the groove (35).

12. The joint of claim 1, wherein said intermediate part (13) is slidable on said planar slide surface (24) of the second prosthetic part (17); and
   wherein said coupling portion include interconnecting means to restrain the movement of the intermediate part with respect to said planar slide surface to movement essentially in the plane of said slide surface (24).

13. The joint of claim 12, wherein said interconnecting means comprise at least one of:
   a tongue-and-groove connection;
   a dovetail connection;
   a T undercut-overlap connection.

14. The joint of claim 1, wherein said condylar portion (19) of the first prosthetic part comprises two condyles (19); and
   wherein said intermediate part comprises two intermediate part elements (13a, 13b), each intermediate part element having a bearing surface (21) for one respective condyle (19).

15. The joint of claim 14, wherein two guide grooves (35) are provided, and individual projecting coupling portions (15) are provided, each, in engagement with a respective guide groove.

16. The joint of claim 15, wherein said guide track grooves are curved, and converge in anterior and posterior positions, and are mirror-symmetrically arranged with respect to a central axis (XS) of the prosthesis.

17. The joint of claim 1, wherein said second prosthetic part (17) is formed with a medial recess (29) of sufficient size to receive at least one of:

an anterior cruciate ligament;
a posterior cruciate ligament, of a knee joint to be replaced.

18. The joint of claim 1, wherein said intermediate part (13) comprises two intermediate part elements (13a, 13b); and
   wherein said first and second guide means comprises two grooves and two coupling portions for, respectively, coupling and guiding the intermediate part elements (13a, 13b) and the second prosthetic part (17); and
   further including a connecting element (49) coupling said intermediate part elements (13a, 13b) together.

19. The joint of claim 18, wherein said connecting element (49) comprises a bridge portion and a holding portion (51) formed with openings receiving said intermediate part elements (13a, 13b), and fitted over said intermediate part elements (13a, 13b).

20. The joint of claim 18, wherein said connecting element (49) comprises a U-shaped bracket or clip (49B); and
   wherein said intermediate part elements (13a, 13b) are formed with openings (53) to receive leg portions (55) of said U-shaped bracket or clip (49B).

21. The joint of claim 1, wherein said first condylar portion comprises a condyle.

22. The joint of claim 1, wherein said condylar portion comprises at least one condyle;
   said bearing surface (21) has essentially the same radius of curvature and is essentially congruent with said condyle; and
   wherein said condyle is convex and the bearing surface is concave.

23. The condylar of claim 1, wherein said first joint portion comprises a concave surface (1621) and said bearing surface comprises a convex, projecting condylar portion (1619), formed on the intermediate part.

* * * * *

UNITED STATES PATENT AND TRADEMARK OFFICE
CERTIFICATE OF CORRECTION

PATENT NO. : 5,282,868
DATED : February 1, 1994
INVENTOR(S) : Andre Bahler It is certified that error appears in the above-identified patent and that said Letters Patent is hereby corrected as shown below:

```
Column 16, line 16 (claim 23), change:

"joint" to --condylar--
        and
 "condylar" to --joint--
```

Signed and Sealed this

Tenth Day of January, 1995

Attest:

BRUCE LEHMAN

Attesting Officer      Commissioner of Patents and Trademarks